United States Patent [19]

Graham

[11] 4,170,234
[45] Oct. 9, 1979

[54] SYSTEM FOR USE WITH ELECTRO-SURGICAL PENCIL

[75] Inventor: Raymond Graham, Mountain View, Calif.

[73] Assignee: Dytek Corporation, Mountain View, Calif.

[21] Appl. No.: 841,035

[22] Filed: Oct. 11, 1977

[51] Int. Cl.² .................. A61B 17/36; A61N 3/06
[52] U.S. Cl. .................. 128/303.14; 128/303.17; 200/6 C; 200/153 K; 200/157; 206/363; 339/99 R
[58] Field of Search .................. 128/303.14, 303.13, 128/303.17, 303.18; 200/153 K, 157, 243, 6 C; 206/363; 339/97 R, 97 P, 98, 99 R

[56] References Cited

U.S. PATENT DOCUMENTS

| 2,720,635 | 10/1955 | Odegaard | 339/99 R |
| 2,929,043 | 3/1960 | Phillips, Jr. | 339/99 R |
| 3,299,241 | 1/1967 | Sayward | 200/153 K |
| 3,720,778 | 3/1973 | Woertz et al. | 339/99 R X |
| 3,799,168 | 3/1974 | Peters | 128/303.14 |
| 3,801,766 | 4/1974 | Morrison, Jr. | 128/303.14 X |
| 3,934,715 | 1/1976 | Antonini et al. | 206/363 X |
| 4,045,650 | 8/1977 | Nestor | 200/153 K |

FOREIGN PATENT DOCUMENTS 1433525 2/1966 France .................. 339/99 R

OTHER PUBLICATIONS

"New! Aid for ECG", Medical Plastics, Inc., 1972.

Primary Examiner—Lee S. Cohen
Attorney, Agent, or Firm—Julian Caplan

[57] ABSTRACT

Electro-surgical pencils are used with a variety of commercially available machines which produce two different types of electrical impulses—one for cutting, the other for cauterizing. In the system of this invention there is a pencil having an electrode received therein (preferably the electrode being reversible to expose two different working ends) and having a finger-actuated, toggle-type switch in the pencil to selectively connect either of the types of electrical impulses to the electrode. A cord having at least three conductors extends from the switch to an adapter which is a multi-contact plug fitting into a matching socket in the machine or permanently attached to the machine. The end of the cord remote from the pencil is received in the adapter and electrical contact with the conductors is expeditiously established. Preferably, the pencil is used with a cup attached to a surgical drape for convenient deposit between uses. The cup, pencil, electrode and cord are preferably disposable and packaged together in a sterile envelope.

10 Claims, 14 Drawing Figures

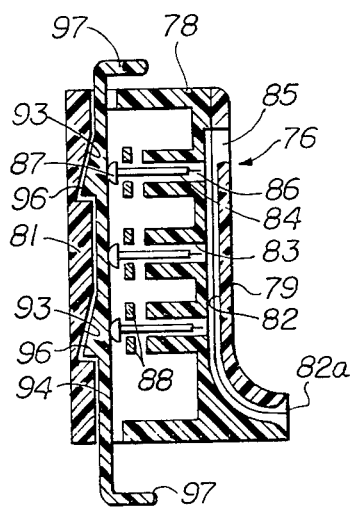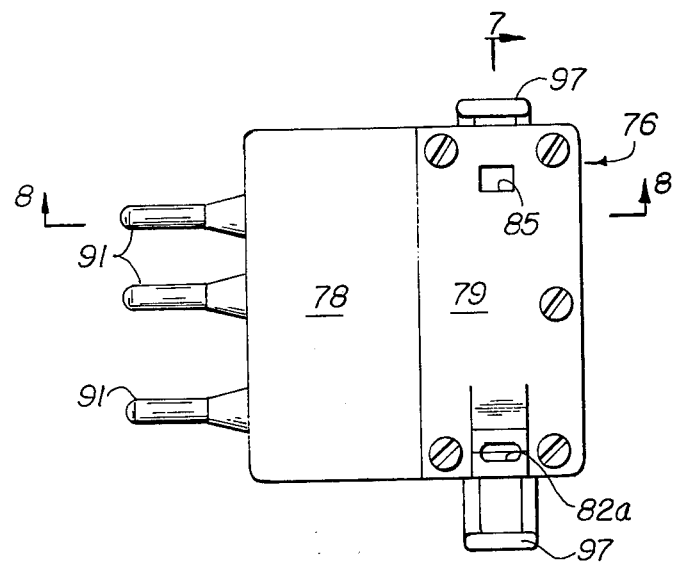
Fig.7 Fig.6
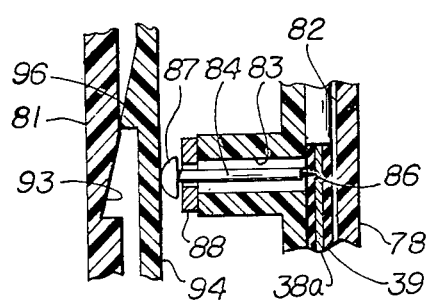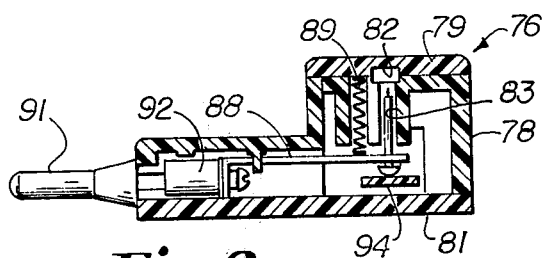
Fig.9 Fig.8
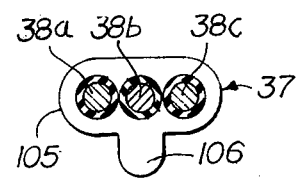
Fig.12
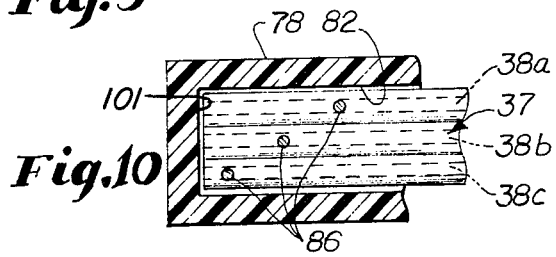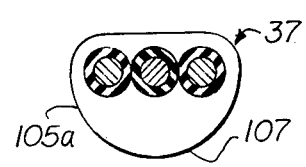
Fig.10 Fig.13
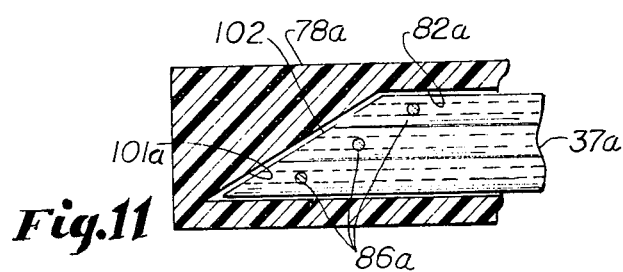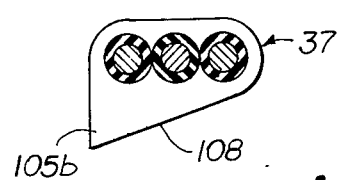
Fig.11 Fig.14

SYSTEM FOR USE WITH ELECTRO-SURGICAL PENCIL

This invention relates to a new and improved system for use with electro-surgical pencil. Reference is made to U.S. Pat. No. 3,934,715, wherein are shown packaged in a sealed sterile package, an electro-surgical pencil, a holder therefor which is attached to a surgical drape during an operation and a cord. The distal end of the cord is attached to an electrical machine which produces electrical impulses of proper voltage, frequency and duration so that the pencil may be used either for cutting or for cauterizing. The present invention provides a switch in the handle of the pencil which is digitally actuated by the surgeon to supply to the blade of the instrument either a cutting or cauterizing current, as selected. An adapter is supplied with the system having either plug elements which fit into one of a variety of commercially available machines or can be permanently attached to said machines. The adapter receives the distal end of the cord attached to the pencil and convenient means is provided, as hereinafter explained, to establish electrical contact with the three or more conductors in the cord. Thus the present invention may be used with a wide variety of different electro-surgical machines.

A principal feature of the invention is the fact that the pencil with its electrode, a holder and the cord may be packaged in a conveniently accessible sterile envelope. The cord is easily attached to the adapter fitted into the machine with no danger that the wires may be reversed and hence without danger that the surgeon may inadvertently manipulate the switch to provide the wrong type of current for the particular use desired.

Another feature of the invention is the fact that a hand held instrument is provided in which the switch which governs the choice of current is incorporated in the handle as contrasted with the presently used foot pedals which are much less convenient and positive in use. The instrument, nevertheless, is light in weight and fits the surgeon's hand properly.

Another feature of the invention is provision of a reversible electrode which fits into the pencil and establishes electrical contact regardless of whether blade or needle end is being used at a particular time.

Still another feature of the invention is the provision of a holder having a sheath which receives the pencil between uses, the sheath being conveniently attached to a surgical drape and having means for cleaning the electrode between uses.

The simplicity and design of the pencil are such that it is quite inexpensive and hence may be disposable, thereby eliminating the necessity of sterilizing between uses. Preferably, the pencil, holder, electrode and cord are sterilized at the factory and transported in a sterile envelope which is not opened until the operation is about to be performed.

Another feature of the invention is provision of an adapter which interfaces with a wide variety of machines for the electrical power source. Provision is made for rapid connection of the cord to the adapter, employing a plurality of insulation piercing pins which establish electrical contact with the conductors in the cord without the necessity of baring the insulation. Thus the insulation-piercing pins are caused to extend and pierce through the insulation of the conductors merely by shifting the position of a grip.

Another feature of the invention is the fact that the cord is so constructed or is so received in the adapter that it will fit only in one particular orientation and hence there is no danger that the pins which pierce the insulation will establish contact with the wrong conductors. Various means are hereinafter described to insure the non-reversal of the conductors.

The use of insulation piercing pins provides a visual indication of use of the cord in the adapter and discourages inadvertent second use of an instrument which has now become non-sterile.

Other objects of the present invention will become apparent upon reading the following specification and referring to the accompanying drawings in which similar characters of reference represent corresponding parts in each of the several views.

In the drawings:

FIG. 6 is a top plan view of an adapter used in the system of FIG. 1.

FIG. 7 is a sectional view taken substantially along the line 7—7 of FIG. 6.

FIG. 8 is a sectional view taken substantially along the line 8—8 of FIG. 6.

FIG. 9 is an enlarged fragmentary view of a portion of the structure of FIG. 7.

FIG. 10 is a further enlarged fragmentary view showing reception of the cord in the adapter.

FIG. 11 is a modification of the structure of FIG. 10.

FIGS. 12, 13 and 14 are cross-sectional views of assymetrical cord shapes which insure proper orientation of the cord in the adapter.

Figure 1:
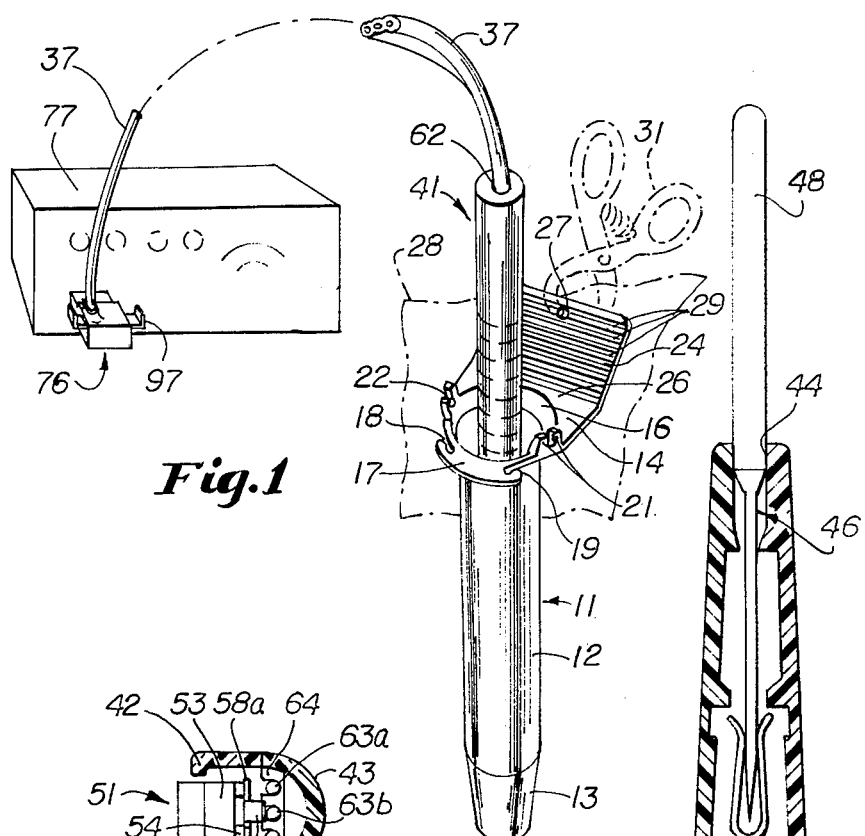
FIG. 1 is a schematic perspective view showing the system of the present invention.
Figure 5:
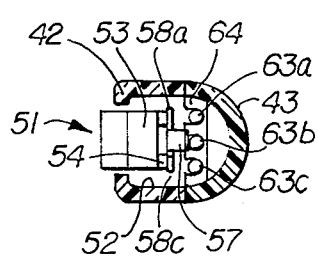
FIG. 5 is a sectional view taken substantially along the line 5—5 of FIG. 2.
Figure 4:
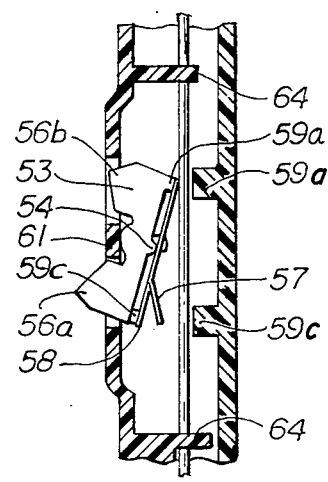
FIG. 4 is a fragmentary view of a portion of FIG. 2 with the switch in a different form of adjustment.
Figure 2:
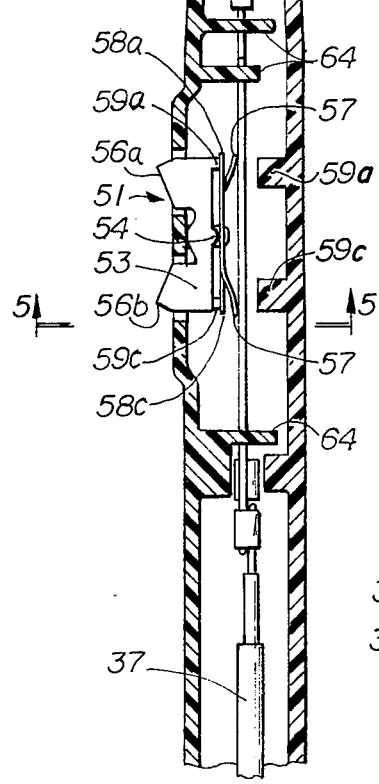
FIG. 2 is an enlarged midsectional view of a portion of the pencil partly broken away to conserve space.
Figure 3:
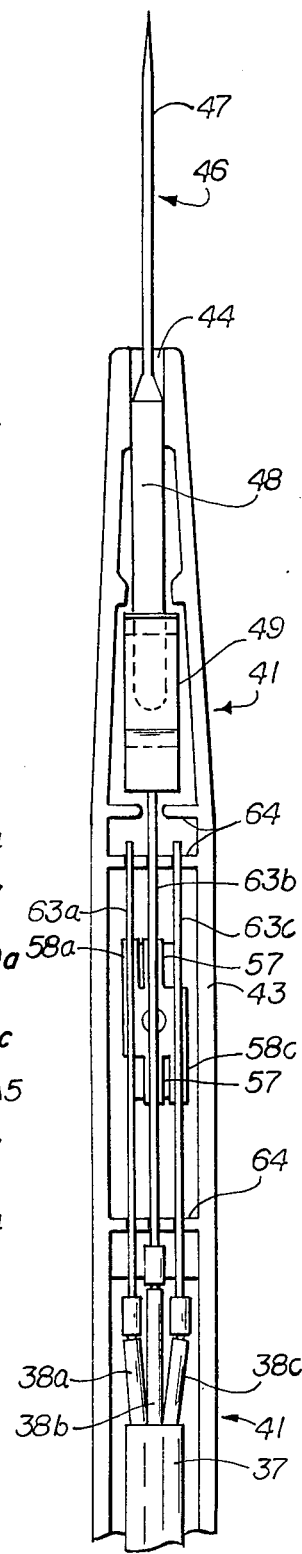
FIG. 3 is a sectional view taken substantially along the line 3—3 of FIG. 2 showing the electrode reversed from the position of FIG. 2.

Directing attention to FIG. 1, many of the components thereof are very similar to those shown in U.S. Pat. No. 3,934,715 and insofar as convenient, the same reference numerals are used to designate corresponding parts. A holder 11 is provided consisting of a cylindrical sheath 12 having a distal end 13 and a transverse flange 14 at the opposite end. Preferably, there is a flared entrance 16 at the top of the sheath 12 to facilitate dropping the instrument into the holder. A lateral extension 17 of flange 14 is provided and on opposite edges of extension 17 are slots 18 with enlargements 19 at the entrance of the slots to retain portions of the cord 37 therein, although such use of the cord is not illustrated in FIG. 1. There are bosses 21 with a slit 22 therebetween at the flared entrance 16 for use in cleaning the blade of the instrument. Opposite extension 17 is a tab 24 connected to flange 14 by a hinge 26. A hole 27 is formed at the remote end of tab 24 to facilitate attachment of tab 24 to a surgical drape 28 by means of a drape clamp 31 or other means. First serrations 29 on the tab 24 facilitate cleaning the blade as an alternate to the use of the bosses 21 and slit 22.

Cord 37 is preferably flat and contains at least three parallel insulated conductors designated herein 38A, 38B and 38C. Such a cord 37 is connected to a source of electric current which provides two different types of impulses, one used for cutting and the other for cauterizing. Each conductor 38 is surrounded by its own insulation 39. The proximal end of cord 37 is received in a handle 41 which is shown in detail in FIGS. 2-5, inclusive. Preferably, the handle 41 comprises top and bottom casing halves 42, 43 suitably secured together after assembly of the elements which are contained therein. At one end of handle 41 is an opening 44 for electrode 46 which is here shown as reversible. One end of electrode 46 has a sharp point 47 and the other end has a relatively flat spatulate blade 48. Other shapes of the opposite ends of a reversible electrode may be used. Further, the electrode may be fixed in the handle. Within the handle 41 is a receiver connector 49 which is of conductive resilient material shaped to hold and establish electrical contact with either end 47 or 48 but to permit the blade to be removed and reversed as desired.

Cord 37 is received in handle 41 through opening 62 in the end opposite opening 44. Incorporated within handle 41 is toggle switch 51 which has a neutral and two contact positions, one for conductor 38a, the other for conductor 38c. A relatively stiff wire or buss 63b is spliced to conductor 38b, extends forwardly down the center of casing half 43, being located therein by slots in transverse partitions 64 and is fixed to receiver 49. Parallel similar busses 63a and 63c are spliced to conductors 38a and 38c, respectively, and extend forwardly, also being located in slots in partitions 64. Switch 51 is retained within a switch chamber 52 in handle 41 and consists of a switch body 53 having finger control projections 56a, 56b from body 53 which extend out of chamber 52 to the exterior of the handle 41 in a location convenient for the surgeon to depress either projection 56a or 56b or neither. On either side at the center of body 53 are fulcrums 54, which assist in causing the body 53 to pivot when one projection 56 is depressed. Fixed to the body 53 is a conductive spring member having upward slanted fingers 57 at either end at the middle and oppositely laterally offset contacts 58a and 58c at either end. In assembled position, contact 58a overlies buss 63a while contact 58c overlies buss 63c. Preferably, body 53 has bosses 59a, 59c at either end overlying contacts 58a, 58c. Thus the fingers 57 bias body 53 to neutral position and at such position neither contact 58 engages buss 63 but fingers 57 continuously contact buss 63b. When projection 56a is depressed, boss 59a presses contact 58a into engagement with buss 63a. Similarly, when projection 56b is depressed, boss 59c presses contact 58c into engagement with buss 63c. Since busses 63a and 63c are connected to relays in the machine which control different types of current, electrode 46 receives different types of current, e.g., for cutting or cauterizing, at the discretion of the surgeon.

As is explained in U.S. Pat. No. 3,934,715, the electrode 46, which is removable from the handle 41 and reversible or the configuration with fixed electrode, the holder 11 and the cord 37 are preferably disposable items which are packaged in a sterile envelope (not shown), sterility being maintained until the envelope is opened in the operating room.

Directing attention now to FIG. 1, the distal end of cord 37 is received in an adapter 76 which is attached to or plugged into a plate 77 of an electro-surgical machine. Details of a preferred adapter are shown in FIGS. 6-9, inclusive. Body 78 is provided with a top cover 79 and bottom cover 81 secured thereto by means of screws. A cord receptable 82 is provided in the body 78, the nurse inserting the distal end of the wire in the flared opening 82a until it contacts the end of receptacle 82 as observed through observation hole 85. In the adapters shown in the drawings, there are three parallel conductors 38a, 38b, 38c in the cord 37, it being understood that more than this number of conductors is sometimes required. In order to establish electrical contact with each of the three conductors, three pin guides 83 are formed in the body 78, each receiving a pin 84 which reciprocates in its guide 83 and having a point 86 at one end and a rounded head 87 at the opposite end. Spring electrical contacts 88 which are bifurcated at their ends adjacent the pins 84 are supported in body 78 and are biased away from cord receptacle 82 by compression springs 89 which fit into appropriate sockets in body 78. Each spring contact 88 is connected to one of the male pins 91 which extend from the body 78 and each said pin 91 is connected to one of the contacts 88 by a connector 92. The number and spacing of the pins 91 depends upon the construction of the machines 77, varying with the various manufacturers. In some machines, pins 91 may be eliminated and wires (not shown) are soldered from contacts 88 to appropriate locations in the machine. However, an adapter 76 is provided for each type of machine and once provided for the machine it will receive a cord 37 each time an operation is performed. In order to facilitate connection of the cord 37 to the pins 91, the inside of the bottom cover 81 is preferably formed with cams 93 and a movable cam actuator 94 (slideable relative to body 78) is formed with cam followers 96 engaging the cams 93. In the position of FIG. 7, the cam followers 96 are in retracted position. At either end of actuator 94 are grips 97. By pushing the grip 97 which is exposed in FIG. 7 inwardly, relative to body 78, the cam followers 96 are brought from the position of FIG. 7 to the position of FIG. 9, moving the actuator to the right and depressing the heads 87 of the three pins 84 so that their points 86 pierce through the insulation 39 of the various conductors and establish electrical contact with the bare wires. Hence the individual conductors of the cord 37 are connected to the appropriate pins 91.

It is important that the cord 37 be received in the receptacle 82 in proper orientation so that the proper pins 91 will be connected to the proper conductors 38a, 38b, 38c. Also, it is important that the spacing between copper conductors in the cord is the same as the spacing between the pins so that electrical contact is made. Alternative ways to ensure the proper connection are illustrated herein. Thus as shown in FIG. 10, the end 101 of the receptacle 82 is square and the inner end of the cord 37 is cut off square. The pin points 86 are spaced and staggered, as shown in FIG. 10. As shown in FIG. 7, the pins are longitudinally spaced apart; and as shown in FIG. 10, the distance of each pin to the side walls of the receptacle 82 is likewise staggered. In the alternative shown in FIG. 11, the end 101a of the body 78a is formed with a bevel and the end 102 of the cord 37a is complementary. The alternative of FIG. 11 prevents the cord from being improperly connected; since if the direction of the bevel is reversed, contact of the pin points 87 will not be achieved.

In FIGS. 12-14, assymmetrical cords 37 are shown. In FIG. 12, a longitudinally extending rib 106 is formed on the assymmetrical cord 105, and the receptacle 82 (not shown in FIG. 11) is so shaped that the rib 106 will fit into the receptacle only in one position of the cord 37. In FIG. 13, the cord 37 has an assymmetrical shape 105a provided by the arched surface 107. Here again, the receptacle 82 (not shown) is shaped complementary, FIG. 14 shows the cord face 105b having a slanted surface 108. It will be understood that the alternatives of FIGS. 10-14 are merely illustrative.

In order to avoid the possibility of adjacent conductors shorting out to each other at the distal-blunt-end of wire 37, an insulating coating is applied to this distal wire end or the insulation of the wire is squeezed over the copper wire end and sealed onto itself to separate and cover the copper wire ends.

In use, the non-sterile operating nurse holds the exterior of the sterile envelope in which the cord 37, handle 41 and holder 11 are packaged. The sterile nurse removes the holder 11 and the handle 41 containing the blade 46. Meanwhile, the non-sterile nurse inserts the distal end of the cord 37 in the adapter 76 and depresses the appropriate grip 97, which causes the pin points 86 to pierce the insulation of the three conductors 38a, 38b, 38c of the cord 37 and establish electrical contact between the adapter 76 and the machine 77 via the pins 91. The holder 11 is clamped to the drape 28 by clamp 31 in a convenient position, depending upon where the incision is being made. The appropriate end of the electrode 46 is exposed (see FIGS. 2 and 3) and the operation is ready to commence. The surgeon grips the handle 41 and his thumb contacts the projections 56a, 56b to connect either buss 63a or 63c and buss 63b, causing the proper impulse to be imparted to the blade 46. The surgeon may manipulate the body 53 to any of its three positions depending upon the requirements at the particular time during the operation. Between uses, the blade 46 is inserted through the opening 16 and the instrument is supported in the sheath 12. From time to time, as a blade 46 must be cleaned, the slit 22 or serrations 29 are used.

When the operation is completed, the grips 97 are reversed in position enabling the cord 37 to be withdrawn from the receptacle 82. Preferably, the cord 37, handle 41, blade 46 and holder 11 are discarded after use. The pin pricks in the end of the cord 37 caused by the points 86 provide a visual indication that the cord 37 has been used and hence that the instrument is nonsterile.

What is claimed is:

1. An electro-surgical pencil comprising an elongated hollow casing having first and second openings at opposite ends of said casing, an electrically conductive electrode fitting into said first opening, a conductive blade receiver in said casing establishing electrical contact with the end of said electrode within said first opening, first, second and third parallel, substantially co-planar stiff wire busses extending longitudinally within said casing, means on said casing for supporting said busses at opposite ends thereof with said busses unsupported at their middles, said second buss electrically connected to said blade receiver, a cord extending into said second opening of said casing having first, second and third insulated conductors connected to said first, second and third busses, respectively, a switch body, said casing formed with slots vicinal the middles of said busses, said body having first and second longitudinally opposed finger control projections extending from the interior of said casing out through said slots said body having fulcrums on either side engaging said casing and enabling said body to pivot when one said projection is manually depressed, a resilient, conductive member formed of a sheet of thin metal fixed to said body, said member having slanted fingers centrally disposed at either end, one said finger continuously engaging said second buss, said member having an integral first contact at a first end laterally offset in a first direction and an integral second contact at a second end opposite said first end laterally offset in a second direction opposite said first direction, said first and second contacts overlying said first and third busses, respectively, said fingers biasing said body to neutral position with neither of said contacts electrically engaging a buss, said body being pivotally mounted in said casing by said fulcrums for a toggle action whereby said first contact engages said first buss when said first projection is depressed, said second contact engages said third buss when said second projection is depressed and neither said first or second contact engages a buss when neither projection is depressed and said body is in neutral position.

2. A pencil according to claim 1 in which said electrode has two different ends and is detachable from said blade receiver so that either end may be exposed through said first opening.

3. An electro-surgical system comprising an electro-surgical pencil comprising an elongated hollow casing having first and second openings at opposite ends of said casing, an electrically conductive electrode fitting into said first opening, a conductive blade receiver in said casing establishing electrical contact with the end of said electrode within said first opening, first, second and third parallel, substantially co-planar stiff wire busses extending longitudinally within said casing, means on said casing for supporting said busses at opposite ends thereof with said busses unsupported at their middles, said second buss electrically connected to said blade receiver, a cord extending into said second opening of said casing having first, second and third insulated conductors connected to said first, second and third busses, respectively, a switch body, said casing formed with slots vicinal the middles of said busses, said body having first and second longitudinally opposed finger control projections extending from the interior of said casing out through said slots, said body having fulcrums on either side engaging said casing and enabling said body to pivot when one said projection is manually depressed, a resilient, conductive member formed of a sheet of thin metal fixed to said body, said member having slanted fingers centrally disposed at either end, one said finger continuously engaging said second buss, said member having an integral first contact at a first end laterally offset in a first direction and an integral second contact at a second end opposite said first end laterally offset in a second direction opposite said first direction, said first and second contacts overlying said first and third busses, respectively, said fingers biasing said body to neutral position with neither of said contacts electrically engaging a buss, said body being pivotally mounted in said casing by said fulcrums for a toggle action whereby said first contact engages said first buss when said first projection is depressed, said second contact engages said third buss when said second projection is depressed and neither said first or second contact engages a buss when neither projection is depressed and said body is in neutral position, and an adaptor having contact means to establish electrical contact with an electrical pulse generating machine, said adaptor having means forming a receptacle for the end of said cord remote from said pencil, at least three pins reciprocable in said adaptor, manually actuated means for moving each of said pins to pierce the insulation of said conductors in the receptacle and establish electrical contact with an individual one of said conductors and said contact means.

4. A system according to claim 3 in which said adaptor and said cord have cooperating means to insure that said cord is receivable in said receptacle in only one orientation of said conductors, whereby said pins always pierce the insulation of the proper conductor.

5. A system comprising an electro-surgical pencil comprising a casing having first and second openings at opposite ends of said casing, an electrically conductive electrode fitting into said first opening, a conductive blade receiver in said casing establishing electrical contact with the end of said electrode within said first opening, means supporting in said casing first, second and third parallel, longitudinal busses, said second buss electrically connected to said blade receiver, a switch in said casing, means for externally digitally manipulating said switch into first, second an neutral positions, said switch having a body, a cord extending into the second opening of said casing having first, second and third insulated conductors connected to said first, second and third busses, respectively, said switch having a conductive member in continuous contact with said second buss, in contact with said first buss when said switch is in first position and with said third buss when said swith is in second position, and out of contact with said first and third busses when said switch is in neutral position, an adaptor having means to establish electrical contact with an electrical pulse generating machine, said adaptor having means forming a receptacle for the end of said cord remote from said casing, at least three pins reciprocable in said adaptor, manually actuated means for moving said pins to pierce the insulation of said conductors in the receptacle and establish electrical contact with said conductors, and means to establish electrical contact between an individual one of said pins and said contact means, and cooperable cam means on said adaptor and said manually actuated means, said manually actuated means being movable between a first and a second position, said manually actuated means engaging ends of said pins remote from said conductors, said cam means moving said manually actuated means from first position with said pins out of contact with said conductors to second position with said pins piercing the insulation of said conductors.

6. A system according to claim 5 which further comprises a holder formed with a sheath receiving said pencil and having one closed end, said pencil and electrode being insertable in and removable from said sheath and said electrode being protected from electrical contact with the exterior when inserted in said sheath, and means on said holder for attachment of said holder to a surgical drape or other convenient hanging means.

7. A system according to claim 6 in which said holder has a flange formed with a boss having a notch for use in cleaning said electrode and also with serrations for use in cleaning said electrode.

8. A system according to claim 6 which further comprises an envelope enclosing and maintaining said pencil, said electrode, said holder and said cord sterile until said envelope is opened.

9. An adaptor to connect a cord for an electro-surgical pencil to an electrical pulse generating machine, said cord having at least two insulated conductors, comprising contact means to establish electrical contact with said pulse generating means, means forming a receptacle for the end of said cord remote from said pencil, at least two pins reciprocable in said adaptor, manually actuated means for moving said pins to pierce the insulation of said conductors when in said receptacle and establish electrical contact with said conductors, and means to establish electrical contact between an individual one of said pins and said contact means, and cooperable cam means on said adaptor and said manually actuated means, said manually actuated means being movable between a first and a second position, said manually actuated means engaging ends of said pins remote from said conductors, said cam means moving said manually actuated means from first position with said pins out of contact with said conductors to a second position with said pins piercing the insulation of said conductors.

10. An adapter according to claim 9 in which said adaptor has means cooperable with means on said cord to insure that said cord is receivable in said receptacle in only one orientation of said conductors, whereby said pins always pierce the insulation of the proper conductor.

* * * * *